United States Patent [19]

Clausen

[11] 4,271,988
[45] Jun. 9, 1981

[54] DISPENSING OF FLUENT MATERIALS

[75] Inventor: Anthony R. Clausen, Johannesburg, South Africa

[73] Assignee: Pitman-Moore, Inc., Washington Crossing, N.J.

[21] Appl. No.: 922,023

[22] Filed: Jul. 5, 1978

[30] Foreign Application Priority Data

Jul. 7, 1977 [ZA] South Africa .................. 77/4095

[51] Int. Cl.³ ............................................. F04B 43/12
[52] U.S. Cl. .................................... 222/214; 222/325
[58] Field of Search ............... 222/214, 206, 101, 102, 222/325; 417/476, 477

[56] References Cited

U.S. PATENT DOCUMENTS

| | | | |
|---|---|---|---|
| 2,662,666 | 12/1953 | Lamport | 222/214 X |
| 2,898,859 | 8/1959 | Corneil | 417/476 |
| 2,909,125 | 10/1959 | Daniels | 222/214 X |
| 3,327,898 | 6/1967 | Farr | 222/214 X |
| 3,386,630 | 6/1968 | Haviland | 417/477 |
| 3,786,683 | 1/1974 | Berman et al. | 417/476 X |
| 3,807,131 | 4/1974 | Samson et al. | 417/476 X |
| 3,908,657 | 9/1975 | Kowarski | 128/278 |
| 3,930,761 | 1/1976 | Barraclough | 417/476 |
| 4,070,725 | 1/1978 | Austin et al. | 417/477 |
| 4,178,138 | 12/1979 | Iles | 417/477 X |
| 4,184,815 | 1/1980 | Casson | 417/477 |

Primary Examiner—Stanley H. Tollberg
Attorney, Agent, or Firm—Donal B. Tobin

[57] ABSTRACT

A dispensing device for use in dispensing measured quantities of fluent material through a resiliently compressible dispensing tube, the device comprising a housing having a cartridge zone for receiving a cartridge having a dispensing tube associated therewith, collapsing structure adapted to be rotatably driven for collapsing a tube located in the cartridge zone in a compression zone, and drive structure for rotatably driving the collapsing structure to displace the compression zone along a compression arc to dispense fluent material through the tube. A dispensing kit comprising a dispensing device as described, a cartridge receivable in the cartridge zone, and a resiliently compressible dispensing tube associated with the cartridge, with the tube having its trailing end connected to a collapsible fluent material container, and having its leading end connected to a dispensing member. A fluent material pack comprising a cartridge receivable in a cartridge zone of a dispensing device, and a resiliently compressible dispensing tube associated with the cartridge; and a cartridge for use with the dispensing device, the cartridge being adapted to have a resiliently compressible dispensing tube associated therewith.

23 Claims, 9 Drawing Figures

DISPENSING OF FLUENT MATERIALS

This invention relates to the dispensing of fluent materials. More particularly, this invention relates to a dispensing device for use in dispensing fluent materials, to a dispensing kit for use in dispensing fluent materials, to a fluent material pack for use with the dispensing device, and to a cartridge for use with the dispensing device.

According to the invention there is provided a dispensing device for use in dispensing measured quantities of fluent material through a resiliently compressible dispensing tube, the device comprising a housing having a cartridge zone for receiving a cartridge having a dispensing tube associated therewith, collapsing means for collapsing a tube located in the cartridge zone in a compression zone, and displacement means for displacing the collapsing means to advance the compression zone along a compression path to dispense fluent material through the tube.

In an embodiment of the invention, the collapsing means may be adapted to be reciprocably displaced so that on its forward motion it will advance the compression zone along a compression path to dispense fluent material, and will then be returned to its initial position relatively to the tube for the following operation.

In this embodiment of the invention, the dispensing device will include bias means to bias the collapsing means back to its inoperative or starting position.

In this embodiment of the invention, the cartridge may be adapted to locate the dispensing tube along a linear or substantially linear path. If desired, however, the cartridge may be adapted to locate the tube along a curved path.

In an alternative embodiment of the invention, the collapsing means may be pivotally displaceable relatively to a tube located in position in the cartridge zone by a cartridge.

Conveniently, the collapsing means may be rotatably displaceable, and the displacement means may be in the form of drive means for rotatably driving the collapsing means.

In this embodiment of the invention, the device may include control means for controlling operation of the drive means, the control means being adjustable to allow the collapsing means to be rotatably driven through a selected angle upon each actuation of the drive means.

Thus, for example, the control means may be adjustable to allow the collapsing means to be rotatably driven through a selected angle of less than 180°, through a selected angle of less than 360°, or through a selected angle of more than 360° upon each actuation of the drive means.

It will be appreciated that, if desired, the control means may be adjustable to allow the collapsing means to be rotatably driven through a plurality of revolutions upon each actuation of the drive means.

Thus by appropriately adjusting the control means, the length of the compression path upon each actuation of the drive means can be adjusted to adjust the quantity of fluent material dispensed by the dispensing device upon each actuation of the drive means.

In an embodiment of the invention, the drive means may comprise a displaceable lever member.

The lever member may, for example, be in the form of a manually displaceable lever member, in the form of a foot operated lever member, or the like.

In this embodiment of the invention, the control means may be adapted to control the extent by which the displaceable lever can be displaced upon actuation thereof, thereby controlling the angle through which the collapsing means is rotatably driven upon actuation of the lever member.

In an alternative embodiment of the invention, the drive means may comprise an electric motor adapted for connection to a suitable power source.

In this embodiment of the invention, the control means may again be operatively associated with the electric motor to control pivotal displacement of the electric motor upon actuation thereof, and thus the angle through which the collapsing means is rotatably driven upon actuation of the electric motor.

The electric motor may be adapted for connection to any suitable power source such as a mains outlet, a vehicle battery, a rechargeable battery mounted on the dispensing device, or the like.

The dispensing device may include adjustment means for adjusting the effective length of the compression path during use.

In an embodiment of the invention, the adjustment means may comprise an adjustable cam member to co-operate with the collapsing means and control the effective length of a compression are during a revolution of the collapsing means.

In one example of the this embodiment of the invention, the adjustable cam member may be adapted to cooperate with the collapsing means to cause the collapsing means to be rotated eccentrically relatively to a tube located in the tube zone, with the adjustable cam member being adjustable to adjust the eccentric movement of the collapsing means and thus the effective length of a compression arc during a revolution of the collapsing means.

In an alternative example of this embodiment of the invention, the collapsing means may include a radially displaceable compression member which is slidably mounted on the collapsing means, and the cam member may be adapted to co-operate with the compression member to control the effective length of a compression arc effected by the compression member.

The compression member may conveniently include bias means operative between it and the cam member to allow for manufacturing tolerances in the wall thickness of a dispensing tube being used in the dispensing device, to combat the compression member becoming jammed against a collapsed dispensing tube if the wall thicknesses of the tube are slightly oversize, and to combat the compression member failing to collapse the tube completely if the wall thicknesses of such a tube are slightly undersize.

In an alternative embodiment of the invention, the adjustment means may comprise means to adjust the effective length of a tube presented to the collapsing means in the cartridge zone.

This may, for example, be achieved by selecting a cartridge in which the effective length of the tube which is associated with the cartridge and which is presented to the collapsing means during use, is as required.

In an embodiment of the invention, the device may have a dispensing tube outlet zone, with mounting means at the outlet zone for mounting a dispensing nozzle on the outlet zone.

The dispensing nozzle may be in the form of an oral dosing nozzle of any conventional type for oral administration of a veterinary remedy or the like. Alternatively, for dispensing a spot-on remedy, the dispensing nozzle may be in the form of a spot-on dispensing nozzle of any conventional type.

The invention further extends to a dispensing kit comprising a dispensing device as described herein, a cartridge receivable in the cartridge zone, and a resiliently compressible dispensing tube associated with the cartridge.

The walls of the housing defining the cartridge zone may conveniently be tapered, and the cartridge may have peripheral walls with a complementary taper to facilitate insertion and withdrawal of the cartridge relatively to the cartridge zone.

The cartridge may conveniently comprise a body portion having a bore defined by a curved compression wall, with the dispensing tube associated with the compression wall for compression against it by the collapsing means during use.

In an embodiment of the invention, the cartridge body portion may have inlet and outlet threading apertures leading to the compression wall, through which the tube is threaded.

The tube may be associated with the cartridge by any convenient means.

In one example of the invention, the dispensing tube may be secured to the compression wall and/or to the inlet and outlet threading apertures by means of a suitable adhesive.

In an alternative example of the invention, the tube may be associated with the cartridge by the inlet threading aperture and, if desired, the outlet threading aperture, having displaceable compression members to engage with the tube.

In an alternative example of the invention, the cartridge and the tube may have complementary engagement formations which are engaged to associate the tube with the cartridge.

Thus, for example, the tube may have an engagement flange extending from it, and the cartridge may have a complementary engagement slot wherein the engagement flange can be frictionally located, located by means of an adhesive, or located by means of a securing panel which can clip into the cartridge to secure the flange of the tube to the cartridge.

Where the tube does have such a securing flange, conveniently only the portion of the tube associated with the cartridge may have the flange, and the remaining parts of the tube connected to either end of that portion may be formed without the flange, or may be formed separately and secured to that portion by means of a suitable adhesive.

The dispensing tube may conveniently be of eliptical cross-section to facilitate collapsing of the dispensing tube by the collapsing means during use.

By having the dispensing tube of eliptical cross-section, it will be appreciated that by varying the length of the major axis of the cross-section of the tube, the volume of fluent material dispensed by the dispensing device during use, can effectively be varied.

Thus depending upon the dosage range of fluent material to be dispensed for each particular fluent material, the cross-sectional area of a dispensing tube may be selected or formed accordingly.

The dispensing tube may conveniently be connected to a collapsible fluent material container. It may conveniently be integrally connected to such a container.

The fluent material container may contain a fluent material to be dispensed, so that the fluent material is housed in the container in a sterile condition when the dispensing tube is sealed by any suitable means, prior to use.

The dispensing tube and fluent material container containing the fluent material, can thus be supplied in a sterile sealed condition.

In an embodiment of the invention, where the fluent material is in the form of an injectable solution or an injectable slurry, a needle or a floating needle may be operatively mounted at the free end of the dispensing tube.

In an embodiment of the invention, the floating needle may be integrally mounted on the tube, for disposal with the tube and fluent material container after use.

The needle may conveniently be in the form of a floating needle for use at a point remote from the dispensing device.

In this embodiment of the invention, the floating needle may conveniently incorporate a one-way valve to combat reverse flow, with the one-way valve being biassed to combat dripping under the action of gravity when the device is not in use.

In an alternative embodiment of the invention, the dispensing tube may be provided with a dispensing nozzle mounted at its free end.

The invention further extends to a fluent material pack for use with a dispensing device as described herein, and comprising a cartridge as described herein receivable in the cartridge zone of the housing of the dispensing device, and a resiliently compressible dispensing tube associated with the cartridge.

The dispensing tube may be associated with the cartridge by any suitable means as hereinbefore described, and the dispensing tube may be associated with a dispensing device, a fluent material pack, and the like as hereinbefore described.

The invention further extends to a cartridge for use with the dispensing device as described herein, the cartridge being in the form of a cartridge as hereinbefore described.

The dispensing device may, in one embodiment of the invention, be in the form of a gun with a handle portion to allow it to be held by hand.

In an alternative embodiment of the invention, the dispensing device may be in the form of a dispensing unit to be placed at a suitable location or to be suspended on the body of an operator.

This invention may have application wherever measured doses of fluent material are to be dispensed from time to time or in short succession.

Thus, for example, the invention can have particular application for dispensing veterinary remedies, pesticides, toxic substances, medicines, dosing materials, and the like.

It will be appreciated that the effective length of a dispensing tube presented to the collapsing means during use, can readily be varied by means of the cartridge.

Thus by varying the effective length of the curved compression wall of the cartridge, the effective length of a tube exposed to the collapsing means, can be varied.

In an embodiment of the invention, the cartridge may have a plurality of outlet zones leading from the curved compression wall, thereby allowing the tube to be threaded through a selected outlet zone for varying the effective length of the tube in contact with the curved compression wall.

Embodiments of the invention are now described by way of example with reference to the accompanying drawings.

Figure 1:
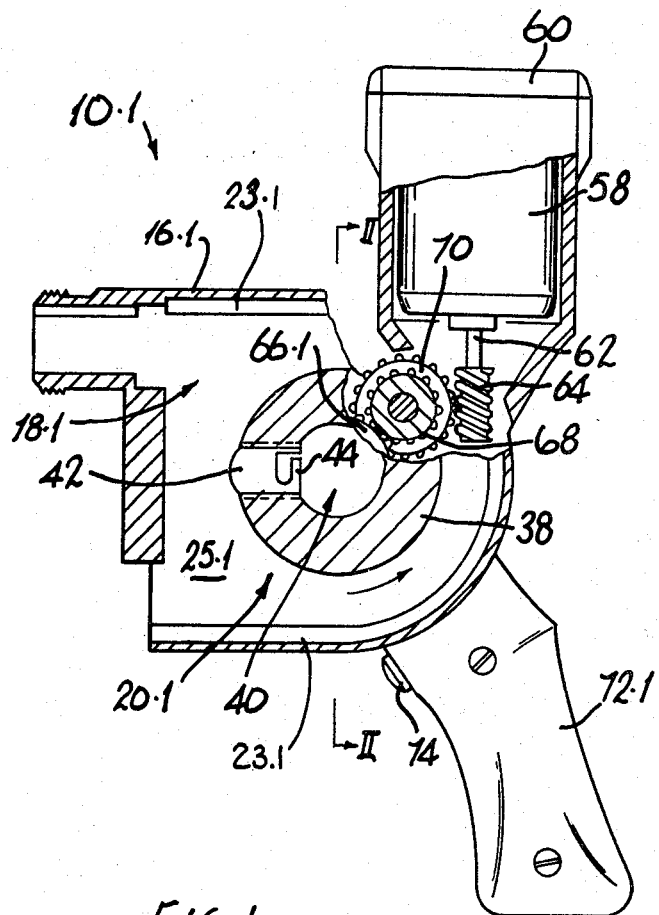
FIG. 1 shows a diagrammatic, fragmentary, partly sectional side elevation along line I—I of FIG. 2, of one embodiment of a dispensing device in accordance with this invention, but with the adjustment means for adjusting the effective length of a compression path during use, omitted for the sake of clarity.
Figure 2:
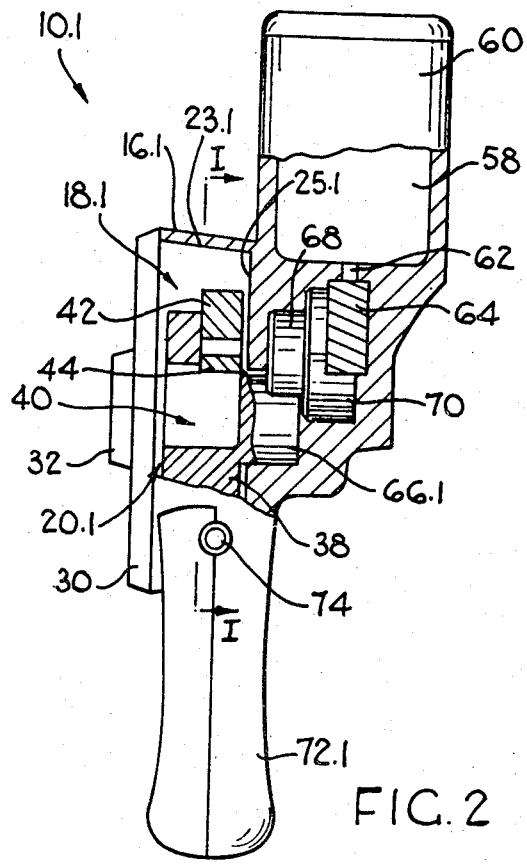
FIG. 2 shows a diagrammatic, fragmentary, partly sectional front elevation along line II—II of FIG. 1, of the dispensing device of FIG. 1, with the compression member of the collapsing means trailing its position as shown in FIG. 1 by 90°, and with the adjustment means for adjusting the effective length of a compression arc during use, again omitted for the sake of clarity.
Figure 5:
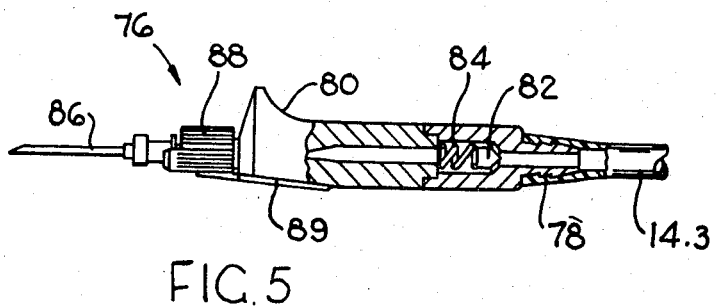
Figure 3:
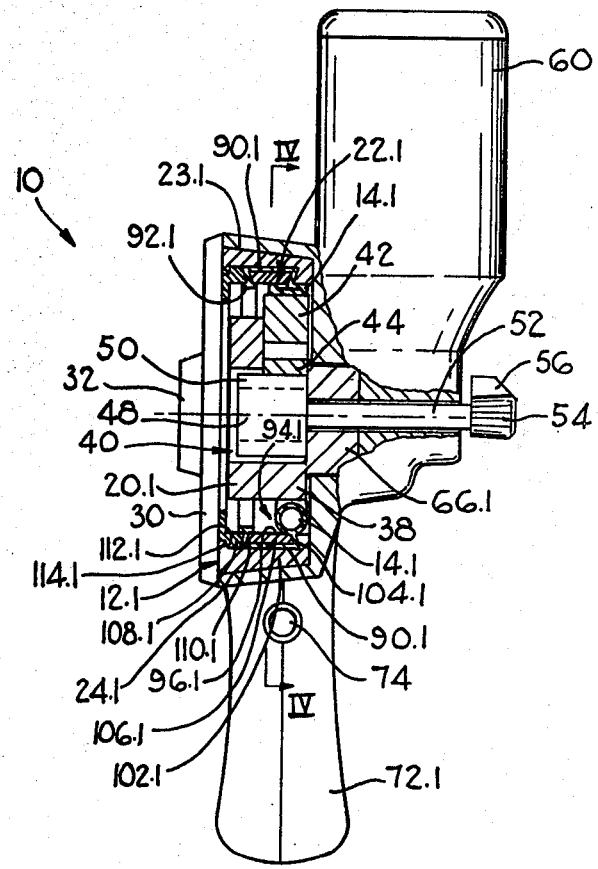
Figure 4:
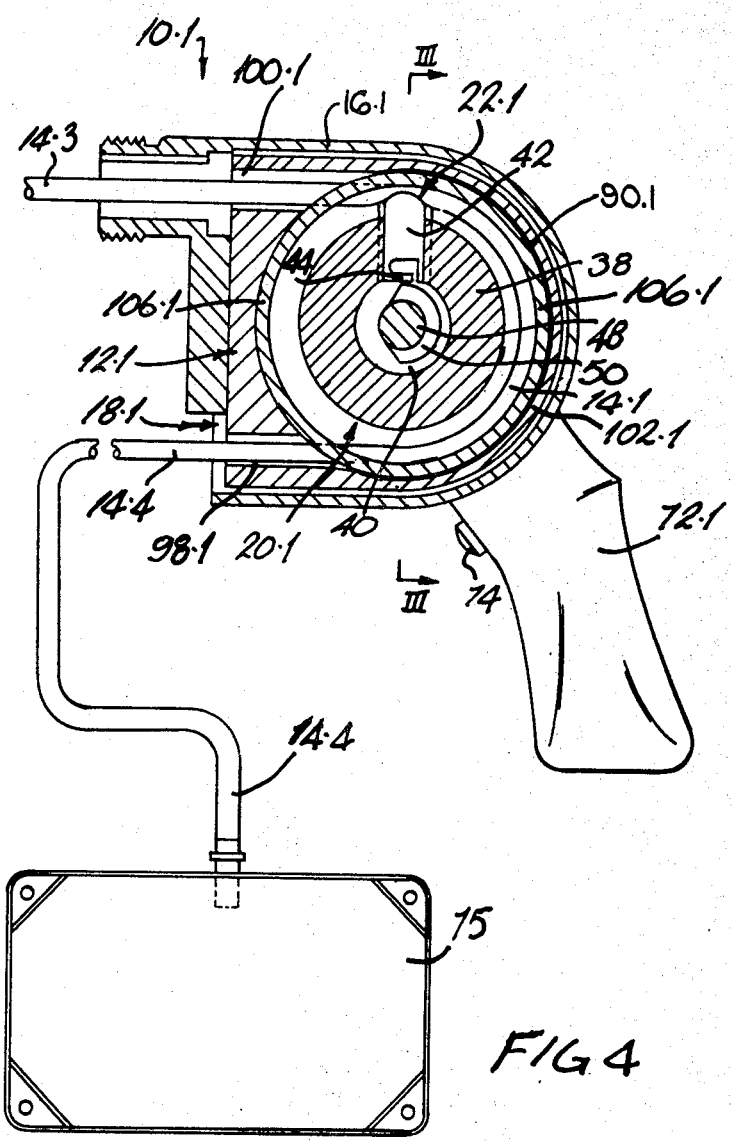
Figure 6:
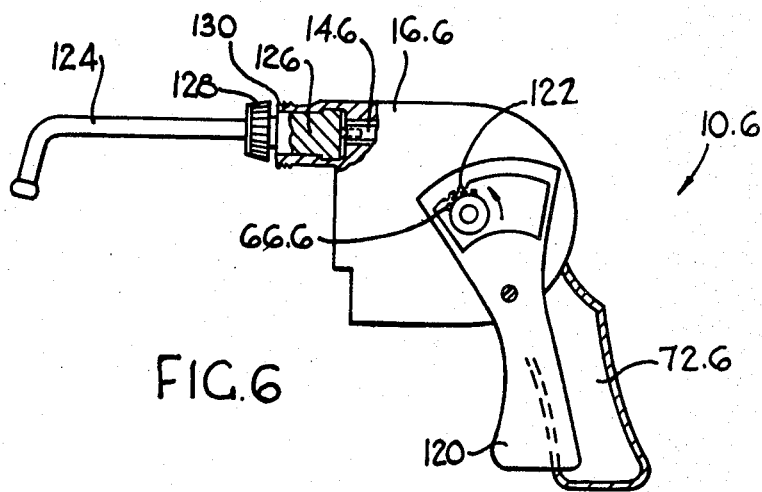
Figure 7:
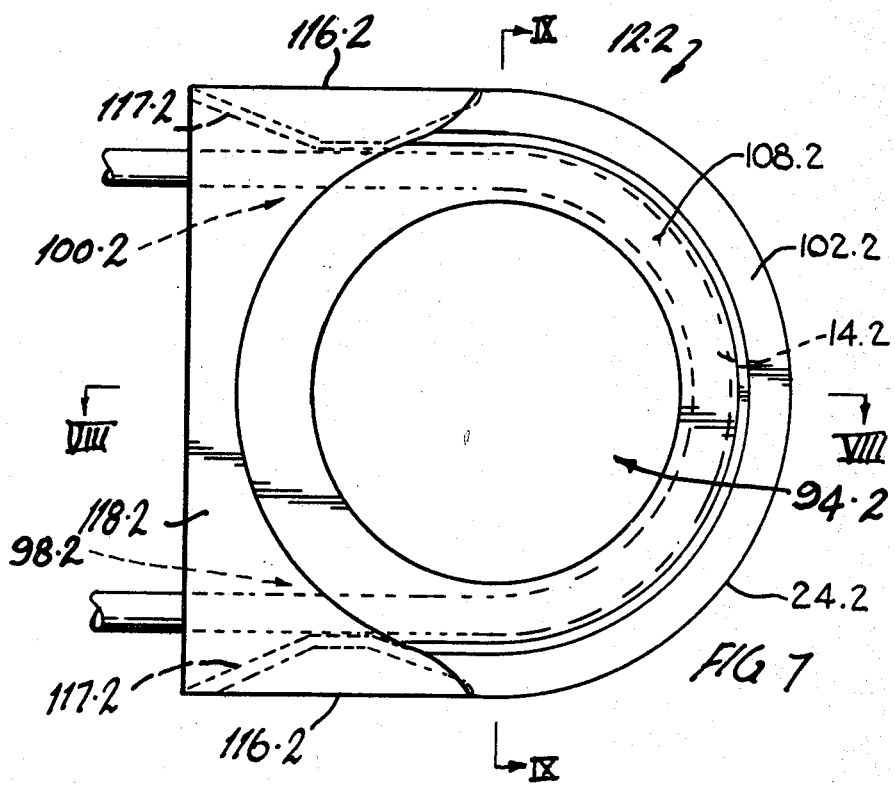
Figure 8:
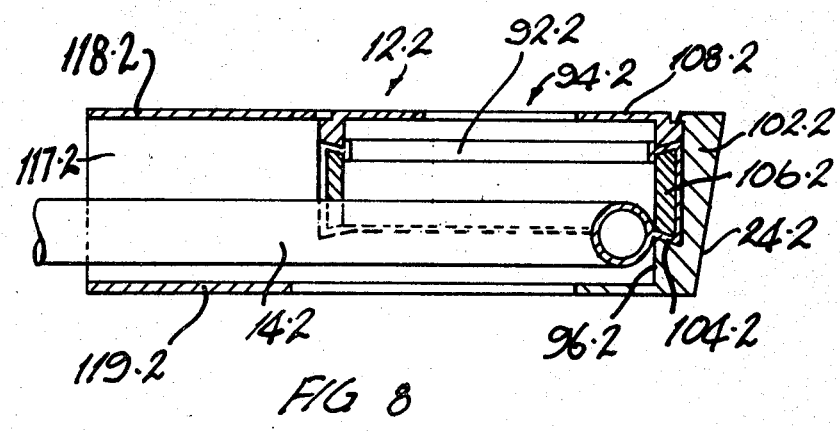
Figure 9:
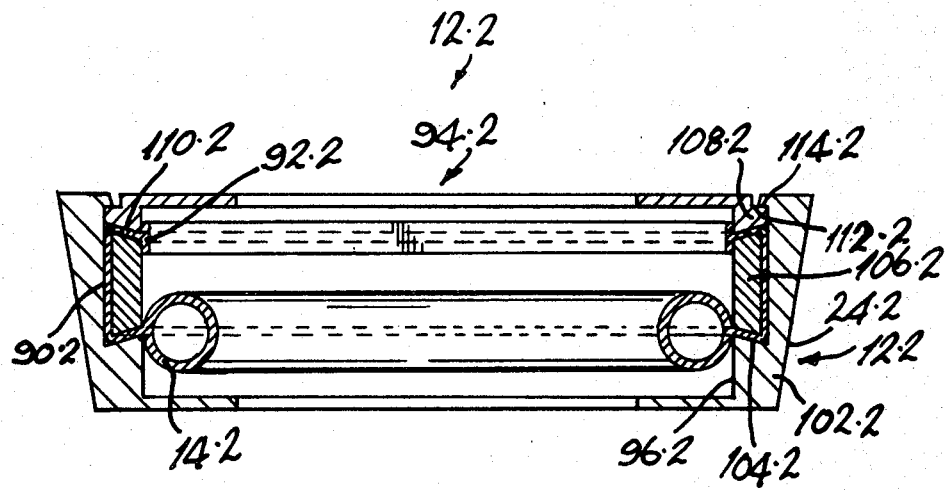

FIG. 3 shows a diagrammatic, fragmentary, partly sectional front elevation along line III—III of FIG. 4 of a dispensing kit in accordance with this invention, comprising the dispensing device as illustrated in FIGS. 1 and 2, but with the adjustment means for adjusting the effective length of a compression arc during use, included therein, and with a cartridge having a dispensing tube associated therewith, removably located in the dispensing device;

FIG. 4 shows a diagrammatic, fragmentary, partly sectional side elevation along line IV—IV of the dispensing kit of FIG. 3;

FIG. 5 shows, to an enlarged scale, a fragmentary, partly sectional plan view of a floating dispensing member attached to the dispensing tube of the dispensing kit of FIGS. 3 and 4, and having a needle mounted thereon;

FIG. 6 shows a diagrammatic, fragmentary, partly sectional side elevation of an alternative embodiment of a dispensing device in accordance with this invention;

FIG. 7 shows, to an enlarged scale, a diagrammatic plan view of an embodiment of a cartridge in accordance with the invention having a dispensing tube mounted thereon;

FIG. 8 shows a diagrammatic sectional side elevation along line VIII—VIII of FIG. 7, of the cartridge; and FIG. 9 shows a diagrammatic sectional plan view along line IX—IX of FIG. 8, of the cartridge.

With reference to FIGS. 1 to 5 of the drawings, reference numeral 10.1 refers generally to a dispensing device for use in dispensing predetermined quantities of an injectable veterinary remedy from a collapsible veterinary remedy container.

In FIGS. 1 and 2 of the drawings, the dispensing device 10.1 is shown alone, whereas in FIGS. 3 and 4 of the drawings, the dispensing device 10.1 is shown loaded with a cartridge having a dispensing tube mounted thereon so that the embodiments illustrated in FIGS. 3 and 4 in fact illustrate the dispensing kit of this invention.

For the sake of clarity, the adjustment means for adjusting the effective length of a compression arc during use, which is in the form of an adjustable cam member has been omitted from FIGS. 1 and 2, but has been included in the dispensing device of FIGS. 3 and 4.

The dispensing device 10.1 comprises a housing 16.1 having a cartridge zone 18.1 for removably receiving a cartridge 12.1 having a dispensing tube 14.1 mounted thereon, as shown in FIGS. 3 and 4 of the drawings.

The dispensing device 10.1 comprises collapsing means 20.1 which is adapted to be rotatably driven relatively to the tube 14.1 to collapse the tube 14.1 in a compression zone 22.1 (as shown in FIG. 3) and to advance the compression zone along a compression arc to dispense the veterinary remedy through the tube 14.1.

The cartridge zone 18.1 is defined by a tapered peripheral wall 23.1 which has a complementary taper to the outer peripheral wall 24.1 of the cartridge 12.1 thereby facilitating loading of the cartridge 12.1 into the cartridge zone 18.1, and removal of the cartridge 12.1 from the cartridge zone 18.1.

The cartridge zone 18.1 is further defined by a base wall 25.1.

As can be seen in FIGS. 2 and 3 of the drawings, the dispensing device 10.1 further includes a removable cover plate 30 having a knob 32 which can be held for applying or removing the cover plate 30.

Once the cartridge 12.1 has been located in position in the cartridge zone 18.1, the cover plate 30 can be fixed to the housing 16.1 to close the cartridge zone 18.1 and firmly locate the cartridge 12.1 in the cartridge zone 18.1.

The collapsing means 20.1 comprises a rotary member 38 having a hollow bore 40.

The rotary member 38 has a radially displaceable compression member 42 slidably mounted thereon for radial displacement relatively to the rotary member 38.

The compression member 42 has opposed flanges along its opposed sides which are slidably received in corresponding slots in the rotary member 38 to allow the compression member 42 to be slidably displaced in the radial direction.

The compression member 42 is formed with a resilient portion 44 which is resiliently flexible to serve the purpose as will be hereinafter described.

The compression member 42 is formed out of a self-lubricating synthetic plastics material to reduce frictional resistance between the compression member 42 and the dispensing tube 14.1 during use.

The dispensing device 10.1 further includes adjustment means for adjusting the effective length of the compression arc during a revolution of the rotary member 38.

The adjustment means comprises an adjustable cam member 48 having a camming surface 50 which extends through an angle of 180°.

The cam member 48 with its camming surface 50 is located within the hollow bore 40 and has an adjustment shaft 52 extending therefrom through a suitable bore in the housing 16.1.

The adjustment shaft 52 terminates in an adjustment knob 54 having a pointer 56.

In use, if the rotary member 38 is rotatably driven with the cam member 48 in the position indicated in FIGS. 3 and 4 of the drawings, the compression member 42 will co-operate with the camming surface 50 so that the camming surface 50 will force the compression member 42 against the tube 14.1 to collapse the tube 14.1 in a compression zone vertically below the central axis of the cam member 48 when the rotary member is rotated in an anti-clockwise direction. Thereafter, the compression zone will be advanced by the compression member 42 through an arc of 180° until the compression member 42 reaches the position vertically above the axis of the cam member 48 as shown in FIGS. 3 and 4 of the drawings.

However, if the adjustable cam member 48 is pivotally displaced through an angle of 90° from the position illustrated in FIGS. 3 and 4 of the drawings, and located in such new position, the cam will only be effective in forcing the compression member 42 against the tube 14.1 to collapse the tube, through an arc of 90°.

The quantity of fluent material dispensed during such a rotation of the rotary member 38 will be half the quantity previously dispensed when the compression arc extends through an angle of 180°.

In this way, by adjusting the position of the adjustable cam member 48 by means of the adjustable knob 54, the quantity of fluent material dispensed on each revolution of the rotary member 38 can be varied as required.

Markings relating to different masses of animals to be treated with a particular veterinary remedy, may be marked on the outside of the dispensing device 10.1 so that by means of the pointer 56, the adjustment knob 54 can be adjusted for an appropriate quantity of fluent material to be dispensed per revolution in relation to the estimated mass of an animal being treated.

It will be noted that the camming surface 50 co-operates with the resilient portion 44 to displace the compression 42 radially outwardly during use.

The resilient portion 44 therefore allows for manufacturing tolerances in the wall thicknesses of the dispensing tube 14.1 to combat the compression member 42 becoming jammed against the collapsed tube if the wall thicknesses of the tube 14.1 are slightly oversize and to combat failure to collapse the tube 14.1 sufficiently if the wall thicknesses thereof are slightly undersize.

The dispensing device 10.1 includes drive means for rotatably driving the rotary member 38.

In the embodiment illustrated in FIGS. 1 to 4 of the drawings, the drive means comprises an electric motor 58 mounted in a motor housing 60 extending upwardly from the housing 16.1. The motor 58 has a drive shaft 62 extending therefrom, with the drive shaft having a gear 64 mounted thereon.

The rotary member 38 has an annular gear 66.1 provided thereon below the hollow bore 40.

The annular gear 66.1 has a bore through which the adjustment shaft 52 slidably extends.

The annular gear 66.1 and the gear 64 are operatively connected by means of a gear train 68 and 70.

The electric motor 58 is adapted for connection to a suitable power source.

The dispensing device 10.1 includes control means (not shown) of any conventional type for controlling operation of the electric motor 58 to allow the electric motor 58 to rotatably drive the rotary member 38 through a selected angle upon each actuation of the electric motor 58.

The control means may therefore be adjusted so that upon each actuation of the electric motor 58, the rotary member 38 is rotatably driven through any angle less than 180°, less than 360°, or through an angle greater than 360°.

Thus by suitably setting the control means, the dispensing device 10.1 can be operated so that a desired quantity of fluent material can be dispensed upon each actuation of the motor 58.

Thus, for example, it can be set so that the rotary member 38 executes a single revolution upon each actuation of the motor 58, or a plurality of revolutions, depending upon the quantity of fluent material to be dispensed on each occasion.

The dispensing device 10.1 includes a handle 72.1 by which it is held for use.

A finger control button 74 is provided on the handle 72.1 for actuating the electric motor 58.

The dispensing tube 14.1 is formed out of a resiliently compressible synthetic plastics material and is of a convenient length for effective use.

The dispensing tube 14.1 has its trailing end 14.4 integrally connected to a collapsible fluent material container 75 as shown in FIG. 4 of the drawings.

The fluent material container 75 contains the veterinary remedy to be dispensed, and can collapse as the veterinary remedy is dispensed thereby ensuring no build-up of reduced pressure in the fluent material container 75 restraining dispensing of fluent material during use.

The dispensing tube 14.1 has its leading end 14.3 connected to a dispensing member 76 in the form of a floating dispensing member as shown in FIG. 5 of the drawings.

The dispensing member 76 is moulded out of a suitable synthetic plastics material, and has a barbed spigot portion 78 for securing it to the leading end 14.3 of the tube 14.1.

To ensure hygienic use of the dispensing member 76, it may conveniently be integrally connected to the dispensing tube 14.1 to combat re-use thereof.

The dispensing member 76 is shaped to be conveniently held by hand, and has a thumb receiving flange 80.

The dispensing member 76 has a valve closure member 82 located within its bore, to combat any reverse flow of fluent material through it.

The valve closure member 82 is lightly biassed by means of a spring 84 to combat dripping of fluent material out of the dispensing member 76 under the action of gravity when it is not in use.

The dispensing member 76 is shown having a conventional needle 86 mounted thereon by means of a conventional type of threaded cap 88.

If desired, a conventional frangible or tamper-proof label 89 can be provided on the threaded cap 88 and the dispensing member 76 so that it will be broken when the threaded cap 88 is removed to unseal the dispensing member 76. It will thus be readily apparent if the member has been opened or tampered with and if there is therefore doubt as to whether or not the veterinary remedy is still in a hygienic and uncontaminated condition.

The dispensing member 76 is thus in the form of a so-called floating needle which can be gripped by hand and forced into a suitable location on an animal, whereafter it can be released while the veterinary remedy is dispensed through the dispensing tube 14.1 by the dispensing device 10.1 of this invention, and into the animal through the needle 86. After the required dose has been dispensed, the dispensing member 76 can be withdrawn and can then be applied to a further animal.

In use, prior to fitting of the needle 86, the dispensing member 76 will be sealed by the threaded cap 88.

Thus the assembly of the fluent material container 75, the dispensing member 76 and the dispensing tube 14.1 with the cartridge 12.1 will be maintained in a sealed hygienic condition for storage and supply to a user.

This provides the advantage that the veterinary remedy can be stored and supplied in a hygienically sealed condition. When required for use, it can readily be fitted into the dispensing device 10.1 for dispensing the veterinary remedy. Fitting of the assembly into the dispensing device 10.1 is facilitated by the cartridge 12.1 which has the dispensing tube 14.1 firmly secured thereto, and is shaped to be securely accommodated in the cartridge zone 18.1.

This arrangement provides the further advantage that since the veterinary remedy does not come into contact with the dispensing device 10.1, it eliminates the need to sterilise the dispensing device 10.1 from time to time.

It is a further advantage of the embodiment as illustrated in these figures of the drawings that once the veterinary remedy contained in the fluent material container 75 has been used, the entire assembly of the dispensing member 76, the cartridge 12.1, the dispensing tube 14.1 and the container 75 can be disposed of. In this way, the inadvertent use of a contaminated remedy will be avoided.

In addition, any wear that may occur on the dispensing tube 14.1 will be negligible because of the short period of time for which the tube is used until the fluent material contained in the container 75 has been dispensed.

This embodiment of the invention as illustrated in these figures of the drawings, provides the further advantage that even where the veterinary remedy is in the form of an abrasive slurry or the like, it will not subject the dispensing device 10.1 to undue wear.

It provides the further advantage that the dispensing device 10.1 can be set means of the adjustable cam member 48 and by means of the control means to provide many variations in the dosages to be dispensed on each occasion during use.

By appropriately setting the dispensing device 10.1, a large variety of veterinary remedies can be effectively dispensed in desired dosages for various animals and for animals of various masses.

The portion of the dispensing tube 14.1 which is associated with the cartridge 12.1 has an engagement flange 90.1 integrally formed therewith for use in securing the dispensing tube 14.1 to the cartridge 12.1.

The engagement flanges 90.1 has a transversely extending shoulder 92.1 provided at its free end.

The cartridge 12.1 comprises a body portion having a bore 94.1 defined by a semi-circular compression wall 96.1 against which the dispensing tube 14.1 is compressed by the compression member 42 during use to dispense fluent material through the dispensing tube 14.1 during rotation of the rotary member 38.

The cartridge 12.1 has inlet and outlet threading apertures 98.1 and 100.1 leading to the compression wall, through which the tube is threaded.

The cartridge 12.1 has an outer wall 102.1 which has an angled shoulder 104.1.

The cartridge further comprises a removable annular clamping ring 106.1 which has its opposed ends tapered for the purpose as will be hereinafter described.

The cartridge 12.1 further includes a removable annular locking ring 108.1.

The annular locking ring 108.1 has a tapered lower surface 110.1, and has an annular shoulder to co-operate with a complementary shoulder 114.1 provided on the outer wall portion 102.1.

Thus to locate the dispensing tube 14.1 in position on the cartridge 12.1, the engagement flange 90.1 can be located on the outer wall, whereafter the annular clamping ring 106.1 can be fitted to the outer wall 102.1, and then the annular locking ring 108.1 can be fitted in position with the annular shoulder 112.1 co-operating with the complementary annular shoulder 114.1. Thus, in this position, the engagement flange 90.1 is firmly clamped to the cartridge 12.1.

In view of the angled shoulder 104.1, the tapered surfaces of the clamping ring 106.1, and the tapered lower surface 110.1 of the locking ring 108.1, the dispensing tube 14.1 will be firmly located on the cartridge 12.1.

It is thus an advantage of the embodiments of the invention as illustrated in FIGS. 3 and 4 of the drawings, that the dispensing tube 14.1 is firmly secured to the cartridge 12.1 and will therefore be firmly located in position in the dispensing device 10.1 to combat axial displacement of the dispensing tube 14.1 with the rotary member 38 during use.

This embodiment provides the further advantage that because of the cartridge 12.1, loading and unloading thereof into the dispensing device 10.1 is facilitated and the dispensing tube 14.1 is held securely in its appropriate position for compression by the compression member 42.

With reference to FIG. 6 of the drawings, reference numeral 10.6 refers generally to an alternative embodiment of a dispensing device to the dispensing device 10.1. Corresponding parts of the dispensing device 10.6 which correspond with those of the dispensing device 10.1, are indicated by corresponding reference numerals except that the suffix '0.6' has been used in place of the suffix '0.1'.

The dispensing device 10.6 has an alternative form of drive means for rotatably driving its rotary member (not shown in FIG. 6).

The drive means comprises a pivotally mounted lever 120 which is associated with the handle 72.6 for manual displacement into the handle 72.6.

The lever 120 has a gear portion 122 to co-operate with the annular gear 66.6 of the rotary member.

The dispensing 10.6 includes a return spring (not shown) to displace the lever 120 back into its inoperative position. It further includes a suitable directional clutch or the like of any conventional type, to release the annular gear 66.6 from the gear portion 122 during return of the lever 120 to its inoperative position after it has been manually compressed into the handle 72.6 during use.

The lever 120 is such and its co-operation with the annular gear 66.6 is such that upon full compression of the lever 120 into the handle 72.6, the rotary member will be rotatably driven through an angle of 360°.

The dispensing device 10.6 further includes a stop member (not shown) provided in the handle 72.6 which can be actuated to limit the movement of the lever 120 and thus adjust the extent by which the rotary member is rotated upon actuation of the lever 120.

The dispensing kit 10.6 is shown having dispensing means in the form of an oral dosing nozzle 124 of conventional type, operatively mounted thereon, with the outlet portion of the dispensing tube 14.6 sealingly connected to the nozzle 124.

The nozzle 124 is located in position by having a locating portion 126 located within a complementary bore in the housing 16.6, and by having a threaded cap 128 to co-operate with a threaded portion 130.

It will be appreciated that, if desired, a nozzle 124 may be mounted in the same way on the dispensing device 10.1.

With reference to FIGS. 7 to 9 of the drawings, reference numeral 12.2 refers generally to an embodiment of a cartridge in accordance with this invention, having a dispensing tube 14.2 mounted thereon.

The cartridge 12.2 corresponds generally with the cartridge 12.1 as illustrated in FIGS. 3 and 4 of the drawings and corresponding parts are indicated by corresponding reference numerals except that the suffix '0.2' has been used in place of the suffix '0.1'.

While the cartridge 12.2 corresponds generally with the cartridge 12.1, it has been drawn to an enlarged scale to illustrate the cartridge more effectively.

The cartridge 12.2 comprises an outer wall portion 102.2 which defines a semi-circular outer peripheral portion for the cartridge 12.2 and then two opposed outer walls 116.2 which are parallel and extend smoothly from the semi-circular portion.

The outer periphery of the outer walls 116.2 and the semi-circular portion are tapered for facilitating loading and unloading of the cartridge 12.2 as hereinbefore described.

The outer wall portion 102.2 defines a semi-circular compression wall 96.2 against which the dispensing tube 14.2 is compressed by the collapsing means during use.

The semi-circular compression wall 96.2 leads to opposed inner walls 117.2.

The cartridge 12.2 includes upper and lower walls 118.2 and 119.2 which are integrally connected to the outer walls 116.2 and the inner walls 117.2.

A gap is thus defined at the leading end of the cartridge 12.2 by the inner walls 117.2 and the upper and lower walls 118.2 and 119.2 through which the dispensing tube 14.2 can be threaded into the compression zone.

As hereinbefore described, the cartridge 12.2 includes an annular removable clamping ring 106.2 which has its opposed ends tapered for securing the engagement flange 90.2 of the dispensing tube 14.2 in position.

The annular clamping ring 106.2 therefore also constitutes a compression wall against which portion of the dispensing tube 14.2 is compressed during use.

As hereinbefore described, the cartridge 12.2 further includes an annular removable locking ring 108.2 which has a tapered lower surface 110.2 having a complementary taper to one of the surfaces of the annular clamping ring 106.2.

The other tapered surface of the clamping ring 106.2 is complementary to that of the angled shoulder 104.2.

As hereinbefore described, the locking ring 108.2 has an annular shoulder 112.2 to co-operate with the complementary shoulder 114.2 provided on the outer wall portion 102.2.

For assembly of the cartridge 12.2, the dispensing tube 14.2 can be positioned against the compression wall 96.2 with the engagement flange 90.2 appropriately positioned in the recess of the outer wall portion 102.2 along its semi-circular curved portion.

Thereafter the annular clamping ring 106.2 can be fitted into position, followed by fitting of the annular locking ring 108.2.

As can be seen in FIG. 8 of the drawings, in this position, the dispensing tube 14.2 is firmly located in position against the compression wall 96.2 and the corresponding compression wall provided by the clamping ring 106.2, by the engagement flange 90.2 being jammed in position by the clamping ring 106.2 and the locking ring 108.2.

The shoulder 92.1 at the free end of the engagement flange 90.2 prevents the engagement flange 90.2 being drawn out of its secured position.

It will be appreciated that the cartridge 12.2 can be effectively moulded in several parts out of a suitable synthetic plastics material, and that the dispensing tube 14.2 can then be readily secured thereto whereupon it will be firmly located in position for use.

The dispensing tube 14.2 may conveniently be extruded with the engagement flange 90.2 and the shoulder 92.2, whereafter appropriate lengths may be cut off to co-operate with the cartridge 12.2, and separately extruded dispensing tubes without the engagement flange 90.2 may then be connected to such sections to provide the leading and trailing ends thereof extending to a fluent material container and to a dispensing device.

The embodiment of the invention as illustrated in FIGS. 7 to 9 of the drawings, provides the advantage that the cartridge can be effectively moulded out of synthetic plastics material, and can be sufficiently inexpensive to allow it to be discarded after use.

It provides the further advantage that the cartridge will firmly locate the dispensing tube 14.2 in position for use to combat any tendency for the dispensing tube to be displaced axially during use, and to combat any tendency for the dispensing tube 14.2 to move out of a position where it is in register with the compression member 42.

It is a further advantage that by means of the cartridge 12.2, effective loading and unloading of the dispensing device 10.1 or 10.2 can be achieved without any risk of incorrect loading.

It will be appreciated that the upper wall 118.2 is shaped to co-operate with the annular locking ring 108.2 to maintain it in its position where it will remain engaged with the outer wall portion 102.2.

It will be appreciated that where the dispensing tube 14.2 is of eliptical cross-section, with the tube positioned so that the major axis of its cross-section is parallel to the compression wall 96.2, collapsing of the tube will be more readily effected.

It will further be appreciated that, in this case, by merely varying the length of the major axis, the cross-sectional area of the dispensing tube 14.2 can be varied and thus the quantity of fluid dispensed during operation, can be varied.

It will further be appreciated that by providing appropriate recesses along portion of the semi-circular compression wall 96.2 and the annular clamping ring 106.2, the effective length of the dispensing tube 14.2 presented to the collapsing means during use, can be altered thereby again allowing for alteration of the dosage dispensed.

Several cartridges having compression walls of differing effective lengths may therefore be provided to allow them to be used for an appropriate remedy where a particular dosage range is required to be dispensed.

I claim:

1. A dispensing device for use in dispensing measured quantities of fluent material through a resiliently compressible dispensing tube, the device comprising a housing having a compression zone and a cartridge zone for removably receiving a unitary cartridge having a dispensing tube engaged therethrough, collapsing means located in the cartridge zone in said compression zone for collapsing said tube, and displacement means for displacing the collapsing means to advance the compression zone along a compression path to dispense fluent material through the tube; and, adjustment means, including an adjustable cam member to cooperate with the collapsing means and control the effective length of a compression path during operation of the collapsing means.

2. A device according to claim 1, in which the collapsing means is pivotally displaceable.

3. A device according to claim 1, in which the collapsing means is rotatably displaceable, and in which the displacement means is in the form of drive means for rotatably driving the collapsing means.

4. A device according to claim 3, including control means for controlling operation of the drive means, the control means being adjustable to allow the collapsing means to be rotatably driven through a selected angle upon each actuation of the drive means.

5. A device according to claim 3, in which the drive means comprises a displaceable lever member.

6. A device according to claim 1, in which the collapsing means includes a displaceable compression member which is slidably connected to the collapsing means, and in which the cam member is adapted to co-operate with the compression member to control the effective length of a compression path effected by the compression member.

7. A device according to claim 1, having a dispensing tube outlet zone and having mounting means for mounting a dispensing nozzle on the outlet zone.

8. A device according to claim 1 further including: a cartridge receivable in the cartridge zone, and a resiliently compressible dispensing tube engaged through the cartridge.

9. A device according to claim 8, in which walls of the housing defining the cartridge zone are tapered, and in which the cartridge has peripheral walls with a complementary taper to facilitate insertion and withdrawal of the cartridge relatively to the cartridge zone.

10. A device according to claim 8, in which the cartridge comprises a body portion having a bore defined by a curved compression wall, and in which the dispensing tube is disposed for engagement with the compression wall for compression thereagainst by the collapsing means during use.

11. A device according to claim 10, in which the cartridge body portion has inlet and outlet threading apertures leading to the compression wall, through which the tube is threaded.

12. A device according to claim 8 further including a dispensing nozzle mounted at the free end of said tube.

13. A device according to claim 8, in which the tube is associated with the cartridge by the tube and cartridge having complementary engagement formations which are enegaged.

14. A device according to claim 8 further including a collapsible fluent material container, integrally connected to said dispensing tube.

15. A pack according to claim 14, in which the fluent material container contains a fluent material to be dispensed.

16. The apparatus of claim 1 wherein said housing peripheral wall tapers outwardly from said housing base wall around at least a portion of its extent.

17. A dispensing device for use in dispensing measured quantities of fluent material through a resilient dispensing tube, said device comprising:
a housing having;
a base wall;
a peripheral wall extending at least partially about the edge of said base wall, and,
a front wall extending from said base wall;
said base wall, said peripheral wall and said front wall defining an open chamber;
a rotatable member having an annular section and a bearing section, said bearing section rollably engaging said housing and supporting said annular section for rotation in said chamber;
drive means for driving said annular section in said chamber;
the peripheral wall of said annular section spaced apart from said housing peripheral wall to define a compression zone therebetween; and,
a compression member projecting from said annular section into said compression zone toward said housing peripheral wall;
wherein said annular section includes:
an aperture extending substantially radially through said annular section wall for receiving said compression member;
cooperative means disposed in said aperture and on said compression member for holding said compression member in said aperture.

18. A dispensing device for use in dispensing measured quantities of fluent material through a resilient dispensing tube, said device comprising:
a housing having;
a base wall;
a peripheral wall extending at least partially about the edge of said base wall; and,
a front wall extending from said base wall;
said base wall, said peripheral wall and said front wall defining an open chamber;
a rotatable member having an annular section and a bearing section, said bearing section rollably engaging said housing and supporting said annular section for rotation in said chamber;
drive means for driving said annular section in said chamber;
the peripheral wall of said annular section spaced apart from said housing peripheral wall to define a compression zone therebetween; and,
a compression member projecting from said annular section into said compression zone toward said housing peripheral wall;
further including a cam member disposed within the open, center portion of said annular section and operatively engaging said compression member;
said cam member having a cam surface cooperatively engaging said compression member over a selectable portion of the rotation of said rotatable member.

19. The device of claim 18 wherein said cam member is pivotably adjustable to control said selectable portion of the rotation of said rotatable member during which said cam surface cooperatively engages said compression member.

20. A dispensing device for use in dispensing measured quantities of fluent material through a resilient dispensing tube, said device comprising;
a housing having;
a base wall;
a peripheral wall extending at least partially about the edge of said base wall; and,
a front wall extending from said base wall;
a base wall, said peripheral wall and said front wall defining an open chamber;

a rotatable member having an annular section and a bearing section, said bearing section rollably engaging said housing and supporting said annular section for rotation in said chamber;

drive means for driving said annular section in said chamber;

the peripheral wall of said annular section spaced apart from said housing peripheral wall to define a compression zone therebetween; and, a compression member projecting from said annular section into said compression zone toward said housing peripheral wall;

a cartridge including a body portion having a bore through a central portion thereof;

a cartridge compression wall extending from said body portion generally concentrically aligned with said bore;

said cartridge adapted to be disposed in said chamber with said compression wall disposed in said compression zone so that said compression member extends into said compression zone toward said compression wall;

a resilient, compressible dispensing tube disposed in said cartridge in position for compression against said compression wall by said compression member, said compression member rotating with said rotatable member;

wherein said cartridge compression wall includes a flange extending therealong and wherein said tube includes a tab extending axially therealong and adapted to be disposed in said compression wall flange;

an annular clamp for holding said tab in said compression wall flange;

the outward edge of said compression wall flange having a rim;

a locking ring cooperatively engaging said rim for holding said clamp in place in said compression wall flange whereby, through the cooperative action of said clamp, locking ring and tab, said tube is held in position in said cartridge.

21. The apparatus of claim 20 wherein said housing peripheral wall tapers outwardly from said housing base wall around at least a portion of its extent, said compression wall includes a taper complementary to the taper in said housing peripheral wall to facilitate insertion and withdrawal of said cartridge relative to said cartridge zone.

22. A fluid dispensing cartridge adapted for ready insertion or withdrawal relative to a dispenser, said cartridge comprising:

a body portion having a bore through a central portion thereof;

a compression wall extending from said body portion generally concentrically aligned with said bone;

a resilient compressible dispensing tube disposed in said cartridge in position for compression against said compression wall;

said compression wall including a tapered portion to facilitate the insertion or withdrawal of said cartridge relative to said dispenser;

said cartridge compression wall includes a flange extending therealong and wherein said tube includes a tab extending axially therealong and adapted to be disposed in said compression wall flange;

an annular clamp for holding said tab in said compression wall flange;

the outward edge of said compression wall flange having a rim;

a locking ring cooperatively engaging said rim for holding said clamp in place in said compression wall flange whereby, through the cooperative action of said clamp, locking ring and tab, said tube is held in position in said cartridge.

23. The device according to claim 20 further including a collapsible, fluent material container integrally connected to said dispensing tube and containing a fluent material to be dispensed.

* * * * *